(12) United States Patent
Rendahl et al.

(10) Patent No.: US 12,358,177 B2
(45) Date of Patent: Jul. 15, 2025

(54) SYSTEM AND METHOD FOR TRACKING LOGS IN A WOOD PROCESSING CHAIN

(71) Applicant: Tracy of Sweden AB, Virserum (SE)

(72) Inventors: Jan-Erik Rendahl, Virserum (SE); Jonny Edvardsson, Virserum (SE)

( * ) Notice: Subject to any disclaimer, the term of this patent is extended or adjusted under 35 U.S.C. 154(b) by 651 days.

(21) Appl. No.: 17/764,165

(22) PCT Filed: Oct. 1, 2020

(86) PCT No.: PCT/IB2020/059190
§ 371 (c)(1),
(2) Date: Mar. 25, 2022

(87) PCT Pub. No.: WO2021/064622
PCT Pub. Date: Apr. 8, 2021

(65) Prior Publication Data
US 2023/0024974 A1    Jan. 26, 2023

(30) Foreign Application Priority Data
Oct. 3, 2019 (SE) .................................. 1930309-8

(51) Int. Cl.
*G06V 20/52* (2022.01)
*B07C 5/14* (2006.01)
(Continued)

(52) U.S. Cl.
CPC ............... *B27B 1/007* (2013.01); *B07C 5/14* (2013.01); *B23D 59/008* (2013.01);
(Continued)

(58) Field of Classification Search
CPC .. B27B 1/007; B27B 1/00; B07C 5/14; B23D 59/008; G01N 21/8986; G01N 33/46;
(Continued)

(56) References Cited

U.S. PATENT DOCUMENTS 10,825,164 B1\* 11/2020 Bolton ................. G06T 7/0006
2005/0040085 A1\* 2/2005 Carman ............. G01N 21/8986
209/576
(Continued)

FOREIGN PATENT DOCUMENTS

AU    2020358453 A1    5/2022
EP    2528716 A1    12/2012
(Continued)

OTHER PUBLICATIONS

Office Action with Search Report issued in SE Patent Application No. 1930309-8 on Mar. 23, 2020, 10 pages.
(Continued)

*Primary Examiner* — Wesley J Tucker
*Assistant Examiner* — Han Hoang
(74) *Attorney, Agent, or Firm* — RC Trademark Company

(57) ABSTRACT

A system (100A) to track logs in a wood processing chain, includes a database arrangement (102) that includes pre-recorded image of a given log, wherein the given log is associated with log identification information. The system further includes a plurality of imaging devices implemented at a sorting station. The plurality of imaging devices (104) is configured to capture a first set of images from at least a first prespecified oblique angle. The system further includes a data processing arrangement (106) that is configured to: identify the given log at the sorting station; compare the at least one pre-recorded image with the captured first set of images at the sorting station in order to find an optimum image from the compared images for identification of the given log; determine a plurality of physical characteristics; and append the log identification information with the determined physical characteristics of the given log.

19 Claims, 4 Drawing Sheets

(51) Int. Cl.
  *B23D 59/00* (2006.01)
  *B27B 1/00* (2006.01)
  *G01N 21/898* (2006.01)
  *G01N 33/46* (2006.01)
  *G06V 10/147* (2022.01)
  *G06V 10/764* (2022.01)
(52) U.S. Cl.
  CPC ......... *G01N 21/8986* (2013.01); *G01N 33/46* (2013.01); *G06V 10/147* (2022.01); *G06V 10/764* (2022.01); *G06V 20/52* (2022.01)
(58) Field of Classification Search
  CPC .... G06V 10/147; G06V 10/764; G06V 20/52; G06V 2201/06; G06V 20/50; G06V 20/60; G06F 18/2413
  See application file for complete search history.

(56) References Cited

U.S. PATENT DOCUMENTS

| | | | | |
|---|---|---|---|---|
| 2005/0161118 A1* | 7/2005 | Carman | ............. | G01N 21/8986 144/403 |
| 2006/0260718 A1* | 11/2006 | Neglay | ................ | B23D 59/008 144/356 |
| 2020/0184620 A1* | 6/2020 | Biernacki | .......... | G01N 21/8851 |
| 2023/0024974 A1 | 1/2023 | Rendahl et al. | | |

FOREIGN PATENT DOCUMENTS

| | | | |
|---|---|---|---|
| EP | 4037883 | A1 | 8/2022 |
| WO | 0213597 | A1 | 2/2002 |
| WO | 2005124323 | A1 | 12/2005 |
| WO | 2018132058 | A1 | 7/2018 |
| WO | 2021064622 | A1 | 4/2021 |

OTHER PUBLICATIONS

International Search Report and Written Opinion of the International Searching Authority issued in International Patent Application No. PCT/IB2020/059190 on Jan. 29, 2021, 15 pages.

Notification Concerning Transmittal of International Preliminary Report on Patentability issued in International Patent Application No. PCT/IB2020/059190 on Apr. 14, 2022, 13 pages.

Examination Requisition issued for Canada Patent Application CA3153449, on Jun. 6, 2023, 04 Pages.

* cited by examiner

SYSTEM AND METHOD FOR TRACKING LOGS IN A WOOD PROCESSING CHAIN

TECHNICAL FIELD

The present disclosure relates generally to a wood processing chain; and more specifically, to systems to track logs in a wood processing chain. Moreover, the present disclosure also relates to methods for tracking logs in a wood processing chain.

BACKGROUND

In timber industries, tagging of a given log is critical in supply chain of timber products. The tagging of the given log allows for identification, categorization and tracking of the given log in the supply chain. Typically, a physical tag is fastened on one end of the given log to indicate a fell place of the log. However, such physical tagging methods are easy to manipulate, and are thus not tamper proof. Currently, certain conventional systems and methods employ one or more imaging devices (such as cameras) at a harvesting stage of the logs to acquire one or more images of the logs. However, such conventional imaging arrangements used for tagging of the logs have problems associated therewith. One of such problems relates to capture of low-quality images of the logs due to severe environment conditions at the harvesting stage (i.e. at the fell place). The low-quality images are inappropriate for identification, categorization and tracking of the log and thereby causes distrust in customers using products made from the logs.

Additionally, the conventional systems are dependent on manual intervention for determining a quality and volume of the given log in downstream stages of the wood processing chain. Consequently, the determination of the quality and the volume of the log are prone to errors.

As a result of the manual inspection of the quality and volume of the given log, a process involved in providing certification to the logs by the conventional systems is cumbersome and prone to errors or human biases.

Therefore, in light of the foregoing discussion, there exists a need to overcome the aforementioned drawbacks associated with the conventional techniques and systems for identifying and tracking of logs in a wood processing chain.

SUMMARY

The present disclosure seeks to provide a system to track logs in a wood processing chain. The present disclosure also seeks to provide a method for tracking logs in a wood processing chain. The present disclosure seeks to provide a solution to the existing problem of manual intervention in tracking of logs in a wood processing chain, and capture of low-quality images of the logs due to severe environment conditions at the harvesting stage (i.e. at the fell place), which adversely affects the identification and tracking of logs in downstream stages of the wood processing chain. An aim of the present disclosure is to provide a solution that overcomes at least partially the problems encountered in prior art, and provides an automated and tamper-proof tracking of logs in the wood processing chain with reliable log identification, log quality determination and log volume measuring without manual intervention.

In one aspect, an embodiment of the present disclosure provides a system to track logs in a wood processing chain, the system comprises:

a database arrangement comprising at least one pre-recorded image of a first end or a second end of a given log at a harvesting site in the wood processing chain, wherein the given log is associated with log identification information;

a plurality of imaging devices implemented at a sorting station, wherein the plurality of imaging devices is configured to:
   capture a first set of images that includes at least one image of the first end and at least one image of the second end of the given log from at least a first prespecified oblique angle with respect to a longitudinal axis in a direction of a length of the given log towards the log, wherein the first prespecified oblique angle is within a defined threshold range; and a data processing arrangement communicatively coupled to the database arrangement and the plurality of imaging devices, wherein the data processing arrangement is configured to:
   identify the given log at the sorting station based on at least the captured first set of images;
   compare the at least one pre-recorded image of the first end or the second end of the given log at the harvesting site with the captured first set of images at the sorting station in the database arrangement, in order to find an optimum image from the compared images for identification of the given log;
   determine a plurality of physical characteristics of the given log at the sorting station based on at least one of the first set of images;
   append the log identification information associated with the given log with the determined plurality of physical characteristics of the given log in the database arrangement and a data memory device having a first machine learning model, wherein the data processing arrangement is configured to train the first machine learning model for identification of a new log when the new log enters the sorting station, wherein the identification is executed by the first machine learning model based on a similarity of features between a newly captured image of a first end or a second end of the new log at the sorting station and the corresponding pre-recorded images of the first end or the second end of the new log captured at the harvesting site.

In another aspect, the present disclosure provides a method for tracking logs in a wood processing chain, wherein the method is implemented in a system comprising a database arrangement, a plurality of imaging devices, and a data processing arrangement, wherein the method comprises:

capturing, by the plurality of imaging devices, a first set of images that includes at least one image of a first end and at least one image of a second end of a given log from at least a first prespecified oblique angle with respect to a longitudinal axis in a direction of a length of the given log towards the log, wherein the first prespecified oblique angle is within a defined threshold range;

identifying, by the data processing arrangement, the given log at the sorting station based on at least the captured first set of images and at least one pre-recorded image of the first end or the second end of the given log at the harvesting site in the wood processing chain;

comparing the at least one pre-recorded image of the first end or the second end of the given log at the harvesting site with the captured first set of images at the sorting station in the database arrangement, in order to find an optimum image from the compared images for identification of the given log;

determining, by the data processing arrangement, a plurality of physical characteristics of the given log at the sorting station based on at least the first set of images;

appending the log identification information associated with the given log with the determined plurality of physical characteristics of the given log in the database arrangement; and training a first machine learning model for identification of a new log when the new log enters the sorting station, wherein the identification is executed by the first machine learning model based on a similarity of features between a newly captured image of a first end or a second end of the new log at the sorting station and the corresponding pre-recorded images of the first end or the second end of the new log captured at the harvesting site.

Embodiments of the present disclosure substantially eliminate or at least partially address the aforementioned problems in the prior art, and enable automated, reliable, and tamper-proof tracking of logs in the entire wood processing chain using log identification information associated with a given log. The present disclosure further addresses the aforementioned problem of the capture of low-quality images of the logs due to severe environment conditions at the harvesting stage (i.e. at the fell place), by identification of the given log and, optionally, replacement of pre-recorded image(s) at the harvesting site with the captured first set of images at the sorting station.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1A:
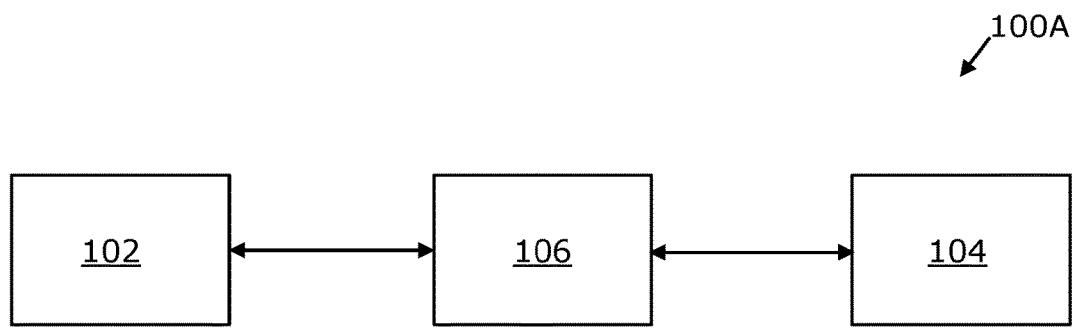
FIG. 1A is a block diagram of a system to track logs in a wood processing chain, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The present disclosure provides an improved system and method to track logs in the wood processing chain in an efficient and tamper-proof manner. The disclosed system ensures reliable log identification and accurate determination of log quality and log volume of a given log without any manual intervention. The system enables to capture images in a sorting stage, which is potentially used to improve the quality of pre-recorded image(s) in a database arrangement (e.g. the pre-recorded image that is captured at the harvesting stage). The system enables assignment of a digital tag (i.e. log identification information) to a given log in the wood processing chain which enables identification, sorting, and tracking of the given log in the wood processing chain. Beneficially the digital tag is implemented with minimal human interference and thereby the system is not prone to human errors. The system enables automated tracking the log at any stage involved in the wood processing chain.

In one aspect, the present disclosure provides a system to track logs in a wood processing chain. The system comprises a database arrangement comprising at least one pre-recorded image of a first end or a second end of a given log at a harvesting site in the wood processing chain, wherein the given log is associated with log identification information. The system further comprises a plurality of imaging devices implemented at a sorting station. The plurality of imaging devices are configured to capture a first set of images that includes at least one image of the first end and at least one image of the second end of the given log from at least a first prespecified oblique angle with respect to a longitudinal axis in a direction of a length of the given log towards the log, wherein the first prespecified oblique angle is within a defined threshold range. The system further comprises a data processing arrangement communicatively coupled to the database arrangement and the plurality of imaging devices. The data processing arrangement is configured to identify the given log at the sorting station based on at least the captured first set of images; compare the at least one pre-recorded image of the first end or the second end of the given log at the harvesting site with the captured first set of images at the sorting station in the database arrangement, in order to find an optimum image from the compared images for identification of the given log; determine a plurality of physical characteristics of the given log at the sorting station based on at least one of the first set of images; and append the log identification information associated with the given log with the determined plurality of physical characteristics of the given log in the database arrangement.

In another aspect, the present disclosure provides a method for tracking logs in a wood processing chain, wherein the method is implemented in a system comprising a database arrangement, a plurality of imaging devices, and a data processing arrangement. The method comprises capturing, by the plurality of imaging devices, a first set of images that includes at least one image of a first end and at least one image of a second end of a given log from at least a first prespecified oblique angle with respect to a longitudinal axis in a direction of a length of the given log towards the log, wherein the first prespecified oblique angle is within a defined threshold range. The method further comprises identifying, by the data processing arrangement, the given log at the sorting station based on at least the captured first set of images and at least one pre-recorded image of the first end or the second end of the given log at the harvesting site in the wood processing chain. In an embodiment, the method further comprises replacing the at least one pre-recorded image of the first end or the second end of the given log at the harvesting site with the captured first set of images at the sorting station in the database arrangement. The system further comprises determining, by the data processing arrangement, a plurality of physical characteristics of the given log at the sorting station based on at least the first set of images. The system further comprises appending the log identification information associated with the given log with the determined plurality of physical characteristics of the given log in the database arrangement.

The present disclosure provides the system to track logs in the wood processing chain. The term "log" as used herein refers to a partial or complete portion of a tree, the log being employed for making various wood-based products. Typically, the log is cylindrical in shape and has a first end and a second end. Typically, each of the first end and the second end of the log is generally circular in shape. Throughout the present disclosure, the term "wood processing chain" herein refers to a sequence of events involved for producing the wood-based products such as furniture, doors, toys, boats, ladder and the like. The wood processing chain comprises events such as felling of trees from a desired and/or designated land such as a forest, separating branches from the trees, making logs from the trees, sorting the logs, storing the logs, and processing the logs to produce the wood-based products. Specifically, the wood processing chain comprises a harvesting stage, a sorting stage, a buffer storage stage, and a sawmill stage. The system to track logs refers to an arrangement to trace the log from the harvesting stage to at least the sorting stage. In an implementation, the system to track logs refers to tracking of the given log from the harvesting stage, to the sorting stage, and further to downstream stages including the buffer storage stage, and the sawmill stage (i.e. when the log enters the sawmill). The logs are tracked to ascertain an origin of the log (e.g. a location of felling of the trees), a quality of the logs, an environment of logs in the processing, an authenticity of the logs and the like. Moreover, the tracking of the logs enables an entity involved in producing the wood-based products in a sustainable way as well as to ensure good quality of wood-based products. The entity refers to an individual, a group of individuals, an organization, a group of organizations, and the like, that produce the wood-based products. Furthermore, end-users associated with procuring the wood-based products are able to acquainted with details related to wood-based products used by them. Consequently, the entity involved in producing the wood-based products and the customers are able to build a trust that the products they are purchasing are legitimate products obtained in sustainable way. In an example, a section of wood-based products produced by the entity is found to be defective. In such a case, the entity may track the log involved in making the wood-based products to determine a root cause, such as whether or not the log was damaged in the wood processing chain, and if found to be damaged than at which stage such damage was introduced, and accordingly a corrective action can be taken.

Moreover, the system comprises the database arrangement comprising at least one pre-recorded image of the first end or the second end of the given log at the harvesting site in the wood processing chain. Throughout the present disclosure, the term "database arrangement" as used herein refers to storage of digital information, such as images related to the given log, regardless of the manner in which the digital information is represented. Optionally, the database arrangement is hardware, software, firmware and/or any combination thereof. In an example, the storage refers to a database system in the form of a table, a map, a grid, a packet, a datagram, files storage, a list or in any other form. The database arrangement includes any data storage software and systems, such as, for example, a server having a relational database.

Optionally, the database arrangement is configured to store batch information that includes the log identification information of each log of a batch of logs. In an exemplary implementation, an unrecorded log entering the sorting station in a batch of logs has no pre-recorded image captured at the harvesting site. In such a case, it is highly likely that the unrecorded log is one of the batch of logs. Thus, in such cases, the unrecorded log is identified by capture of a new image of the unrecorded log and associating it with the batch information of neighbouring logs in the batch of logs in the database arrangement, such as the batch information of the given log of this disclosure. In this way, a new identity is assigned to the unrecorded log that has no pre-recorded image. Thus, in this case, the captured new image for the unrecorded log is stored in the database arrangement at the sorting stage. Thus, in such cases, the data processing arrangement is configured to re-identify the unrecorded log in downstream stages, such as in the buffer storage stage or the saw mill stage, by use of the captured new image in a given stage, the pre-recorded image in previous stage (e.g. harvesting or sorting stage) and/or optionally the batch information.

Throughout the present disclosure, the term "harvesting site" as used herein refers to a place and an environment where trees in a forest are processed to produce the logs. It will be appreciated that, the harvesting site involves felling of the trees, delimbing branches of the trees to produce the logs, and transporting the logs to subsequent stages in the wood processing chain. The term pre-recorded image refers to an image of the given log captured at the stage after a given tree is harvested and processed into the given log. The pre-recorded image is captured via an image capturing device such as a camera. Optionally, the pre-recorded image is captured by the aforementioned entity. More optionally, the pre-recorded image is captured by a feller. Optionally, the feller captures the pre-recorded images by placing the image capturing device close to the first end (front end that is cut transversely that is orthogonal to the longitudinal axis of the log) and the second end (rear end that is cut transversely that is orthogonal to the longitudinal axis) of the given log. In other words, the first end of the given log refers to transversely cut front end (e.g. the cut front end in which annular rings or growth rings are visible). The second end of the given log refers to the transversely cut rear end (the cut rear end in which annular rings or growth rings are visible). In an example, an angle-of-capture of the given log in the at least one pre-recorded image is more than 20 degrees. Typically, the pre-recorded image captured by the feller is not of a good quality as a result of the environment at the harvesting site. In an example, the pre-recorded image is a low-resolution image.

Moreover, the given log is associated with log identification information. Throughout the present disclosure, the term "log identification information" as used herein refers to data related to the given log which enables identification of the given log in subsequent stages of the wood processing chain. Moreover, the identification of the given log enables tracking of the given log. Optionally, the log identification information comprises data such as a unique identifier (ID) assigned to a given log, and associated data, such as at least one image of an end of the given log captured at the harvesting site. Optionally, the log identification information includes a location (Global Positioning System coordinates) of harvesting site of the given log, date and time of felling of the tree from which the given log is derived, or a feller identity who was involved in felling and cutting of the tree. The log identification information is stored in the database arrangement.

Moreover, the system comprises the plurality of imaging devices implemented at a sorting station. Throughout the present disclosure, the term "imaging device" refers to an image-capture device or an image sensor that is configured operable to detect and process light from the sorting station, so as to capture a given image of an environment of the sorting station. Specifically, the imaging device is a camera. Each imaging device of the plurality of imaging devices is employed to capture a different environment in the sorting station. Optionally, the position of each imaging device of the plurality of imaging devices is fixed in the sorting station.

According to an embodiment, the system further comprises a conveyor on which the given log moves in the sorting station. The term "conveyor" as used herein refers to a moving belt which enables movement of the given log from one position to another position in the sorting station. Optionally, the conveyor comprises one or more shafts along which the belt moves. Optionally, the one or more shafts are further connected to motors to provide rotatory movement of the shaft. In an example, a clockwise movement of the motors enables the one or more shafts to move the given log in a forward direction in the sorting station. In such a case, an anti-clockwise movement of the motors enables the one or more shafts to move the given log in a backward (reverse) direction in the sorting station. Optionally, the plurality of imaging devices is positioned above a plane of the conveyor. Consequently, the plurality of imaging devices is operable to capture the images of the given log from a specified position.

Moreover, the plurality of imaging devices are configured to capture the first set of images that includes at least one image of the first end and at least one image of the second end of the given log from at least the first prespecified oblique angle with respect to the longitudinal axis in the direction of the length of the given log, wherein the first prespecified oblique angle is within the defined threshold range. It is to be understood that the log may be turned around in transit from the harvester to the sorting station, or it may enter the sorting station either wide end first or narrow end first. The given log is placed on the conveyor along the length of the given log. In other words, a given log is placed in a way that the length of the given log (i.e. the longitudinal axis of the given log) is along the direction of movement of the conveyor. The first prespecified oblique angle, which by the earlier definition is an acute angle, is the optical alignment of the imaging device relative to the longitudinal axis. The same or different angles may be used to capture the at least one image of the first end and the least one image of the second end of the given log in the first set of images. The defined threshold range is greater than 5 degrees and less than 45 degrees, preferably not less than 10 degrees and not greater than 20 degrees.

In an embodiment, the system further comprises a set of sensors to detect the given log on the conveyor. The sensors of the set of sensors are communicatively coupled to respective imaging devices of the plurality of imaging devices. Examples of the set of sensors include, but are not limited to photosensors, electronic sensors or mechanical sensors or a combination which provide signals to each imaging device of the plurality of imaging devices on detection of the given log on the conveyor. Moreover, based on the detection of the given log, each imaging device of the plurality of imaging devices may be activated at a different timepoint and hence operable to capture the first set of images. Optionally, the set of sensors is positioned at a fixed position below the conveyor. More optionally, the set of sensors is positioned at a fixed position above the conveyor. In an example, each sensor of the set of sensors is an infrared sensor which continuously transmits infrared light. In such a case, the set of sensors detects the given log upon obstruction of the infrared light by the given log. In another example, each sensor of the set of sensors is a load cell which enables detecting the given log based on detecting a weight of the given log.

In an embodiment, the plurality of imaging devices is further configured to capture the second set of images of the given log from the second angle that corresponds to the angle-of-capture of the given log in the at least one pre-recorded image at the harvesting site. The second set of images includes the first and the second end of the given log. The second angle at the sorting station is similar to the angle-of-capture of the given log at the harvesting station to enable identification of the given log at the sorting station. Optionally, the pre-recorded image of the given log depicts features (e.g. annular rings in the transversely cut ends, saw cuts, knots or irregularities of tree growth) associated with the given log. Optionally, the second set of images also depicts similar features associated with the given log. Optionally, the features in the second set of images are matched with the features in the pre-recorded images in order to find an optimum image from the compared images for identification of the given log at the sorting station. Optionally, the features used to identify the log are typically present in only a portion of a whole image. Optionally, the second set of images is captured by the plurality of imaging devices.

The plurality of imaging devices is configured to capture the second set of images when the first end (or the second end) of the given log is in the vicinity to the plurality of imaging devices. In an implementation, images of the second set of images of the first and second end of the given log are captured at a distance (from end of log to imaging device) that is less than the distance of the first and second end of the given log when the first set of images are captured. In an example, the second angle is more than 20 degrees.

According to an embodiment, each of the first set of images and the second set of images captured by the plurality of imaging devices is of a good quality (i.e. having an image quality level that is greater than a defined threshold). In an example, each of the first set of images and the second set of images is a high-resolution image without any distortion.

According to an embodiment, the given log moves on the conveyor in the sorting station at the time of capture of the first set of images and the second set of images. Optionally, the conveyor moves the given log in different positions such as a first given position, a second given position, a third given position and a fourth given position. The first set of images (i.e. image 1 and 4) that are captured, for example, in less than 20-degree angle, at the first given position (captures front end) and the fourth given position (captures rear end) of the given log on the conveyor at the sorting station. Similarly, the second set of images (i.e. image 2 and 3) are captured from an angle mimicking the pre-recorded image(s) captured at the harvesting site at the second given position and the third given position on the conveyor at the sorting station.

According to an embodiment, the system further comprises the set of sensors, wherein a first imaging device of the plurality of imaging devices is positioned at a first location at the sorting station, and wherein the first imaging device at the first location is activated to capture a first image of the first set of images when the first end of the given log passes a first sensor of the set of sensors at the time of movement along a conveyor, wherein the first image includes the first end of the given log. The first image corresponds to the at least one image of the first end of the given log in the first set of images. In an example, a conveyor of a length 100 metres moves a given log from left end of the conveyor to right end of the conveyor and the first imaging device is positioned at a first location such as 20 metres from the left end of the conveyor. In such a case, upon the given log passing the first sensor, the first sensor is configured to send a signal to the first imaging device to capture the first image of the first end of the given log. In such a case, the first image is captured at a first prespecified oblique angle, for example, 20 degrees or an angle less than 20 degree.

According to an embodiment, a second imaging device of the plurality of imaging devices at a second location at the sorting station is configured to capture a second image that corresponds to one of the second set of images when the first end of the given log further passes a second sensor of the set of sensors at the time of movement along a conveyor, wherein the second image includes the first end of the given log. In an example, a conveyor of a length 100 metres moves a given log from left end of the conveyor to right end of the conveyor and the second imaging device is positioned at a second location such as 40 metres from the left end of the conveyor. In such a case, upon the given log passing the second sensor, the second sensor is configured to send a signal to the second imaging device to capture the second image of the first end of the given log.

According to an embodiment, a third imaging device of the plurality of imaging devices at a third location at the sorting station is configured to capture a third image that corresponds to one of the second set of images when the second end of the given log further passes a third sensor of the set of sensors at the time of movement along the conveyor, wherein the third image includes the second end of the given log. In an example, a conveyor of a length 100 metres moves a given log from left end of the conveyor to right end of the conveyor and the third imaging device is positioned at a third location such as 60 metres from the left end of the conveyor. In such a case, upon the given log passing the third sensor, the third sensor is configured to send a signal to the third imaging device to capture the third image of the second end of the given log.

According to an embodiment, a fourth imaging device of the plurality of imaging devices at a fourth location at the sorting station is configured to capture a fourth image that corresponds to the at least one image of the second end from the first set of images when the second end of the given log further passes a fourth sensor of the set of sensors at the time of an exit from the sorting station, wherein the fourth image includes the second end of the given log. In an example, a conveyor of a length 100 metres moves a given log from left end of the conveyor to right end of the conveyor and the fourth imaging device is positioned at a fourth location such as 80 metres from the left end of the conveyor. In such a case, upon the given log passing the fourth sensor, the fourth sensor is configured to send a signal to the fourth imaging device to capture the fourth image of the second end of the given log. The fourth image is captured at the time of the exit of the given log from the sorting station. In such a case, the fourth image is captured at the first prespecified oblique angle, for example, 20 degrees or an angle less than 20 degrees.

Furthermore, the system comprises the data processing arrangement communicatively coupled to the database arrangement and the plurality of imaging devices. Throughout the present disclosure, the term "data processing arrangement" as used herein relates to programmable and/or non-programmable components configured to execute instructions for storing, processing and/or sharing data and/or setting of instruction. Optionally, the data processing arrangement may include, for example, a component included within an electronic communications network. Additionally, the data processing arrangement includes one or more data processing facilities for storing, processing and/or sharing data and/or setting of instruction. Furthermore, the data processing arrangement comprises hardware, software, firmware or a combination thereof. Optionally, the data processing arrangement includes functional components, for example, a processor, a memory, and a network interface (e.g. a transceiver). The data processing arrangement is communicatively coupled to the database arrangement and the plurality of imaging devices via wired or wireless connections or a combination thereof.

Moreover, the data processing arrangement is configured to identify the given log at the sorting station based on at least the captured first set of images. The data processing arrangement is configured to compare the at least one of the captured first set of images or the second set of images with the at least one pre-recorded image of the first end or the second end of the given log stored in the database arrangement. Optionally, the data processing arrangement comprises image analysis software for comparison of the aforesaid images. Optionally, at least one of the captured first set of images or the second set of images depicts the aforementioned features associated with the given log. Notably, the features in the at least one of the captured first set of images or the second set of images are compared with the features in each of the pre-recorded images of the first end or the second end of the given log. In an example, the features associated with the given log comprise a pattern such as growth rings which may be distinct for each tree. In another example, the features associated with the given log comprise a combination of growth rings, saw cuts, knots, irregularities in tree growth, colour, size, or any human made pattern such as a hallmark which may be distinct for each log.

Furthermore, the data processing arrangement is configured to compare the at least one pre-recorded image of the first end or the second end of the given log at the harvesting site with the captured first set of images at the sorting station in the database arrangement, in order to find an optimum image from the compared images for identification of the given log. The comparison may be based upon a feature that occurs in only a small region of the image, as this may be the only feature that can be used to positively identify the log. The data processing arrangement is further configured to replace the at least one pre-recorded image of the first end or the second end of the given log at the harvesting site with the optimum image, if different, in the database arrangement. In performing this replacement, the pre-recorded image is not necessarily discarded from the database arrangement. However, the captured first set of images are preferably set to be the default option of images that are used subsequently in tracking the log. As mentioned previously, the at least one pre-recorded images of the first end or the second end of the given log is potentially not of good quality (i.e. sometimes there is potentially poor clarity in images or comprises unwanted artefacts) and the first set of images is of good quality. Consequently, the at least one pre-recorded image of the first end or the second end of the given log captured at the harvesting site is replaced with the first set of images of the first end or the second end of the given log captured at the sorting station respectively. The database arrangement thereby comprises good quality images of the given log, which enables downstream retrieval of images, identification, and tracking with increased accuracy and reliability. In an example, the database arrangement comprises images of high resolution without any distortion or artefacts.

Moreover, the data processing arrangement is configured to determine the plurality of physical characteristics of the given log at the sorting station based on at least one of the first set of images. The term "physical characteristics" refers to attributes of the given log which are useful for sorting and categorization of logs in wood processing chain, for making wood-based products. Notably, each wood-based product requires logs of specific characteristic to segregate the logs for making different wood-based products.

According to an embodiment, the data processing arrangement is further configured to determine a length and/or volume of the given log at the sorting station based on the first set of images that are captured from the first prespecified oblique angle with respect to the longitudinal axis in the direction of the length of the given log towards the log, wherein the determined length and/or volume is one of the plurality of physical characteristics of the given log. Optionally, the volume is determined based on the first set of images and the first prespecified oblique angle. More optionally, the volume is determined based on the combination of the first set of images captured at the first prespecified oblique angle and the second set of images captured at the second angle. Optionally, the data processing arrangement is configured to determine the diameter of first end and the second end of the given log; and the length of the given log. In an example, the length of the given log is generally available in the database arrangement and is retrieved to determine the volume of the given log. Alternatively, the length of the given log is potentially measured in the sorting station. Moreover, based on the diameter of the first end and the second end, and the length, the volume of the given log is determined by the data processing arrangement. The volume of the logs is determined to enable segregation of the logs based on their volume and corresponding usage for making wood-based products and for buffer storage purposes. In an example, a given log having a 1 cubic metre volume is employed for making a first wood-based product and a given log having a 2 cubic metre volume is employed for making a second wood-based product.

According to an embodiment, the data processing arrangement is further configured to determine a log quality level of the given log at the sorting station based on at least one of the first set of images or the second set of images, wherein the determined log quality level is one of the plurality of physical characteristics of the given log. The log quality level of the logs is determined to enable segregation of the logs based on their log quality and corresponding usage for making wood-based products. In an example, a given log having a log quality level of 9 is employed for making a first wood-based product and a given log having a log quality level of 6 is employed for making a second wood-based product. In another example, a log quality in the range of 6-10 is good quality logs and a log quality in the range of 1-5 is average quality logs, not suitable for high-end products but suited for other purposes.

According to an embodiment, the system further comprises the data memory device having a first machine learning model, wherein the data processing arrangement is further configured to train the first machine learning model for identification of a new log when the new log enters the sorting station, wherein the identification is executed by the first machine learning model based on a similarity of features between a newly captured image of a first end or a second end of the new log at the sorting station and corresponding pre-recorded image(s) of the first end or the second end of the new log captured at the harvesting site. The term "data memory device" refers to storage device, such as read only memory (ROM), or a combination of the ROM and a random-access memory (RAM). Optionally, the data memory device is hardware, software, firmware and/or any combination thereof. Throughout the present disclosure, the term "machine learning model" refers to any mechanism or computationally intelligent system that employs one or more algorithms to generate an output, without being explicitly programmed therefor. The output generated by the machine learning model undergoes correction to obtain desired level of reliability and efficiency. Typically, examples of the different types of machine learning algorithms, depending upon the training dataset employed include, but are not limited to: supervised machine learning algorithms, unsupervised machine learning algorithms, semi-supervised learning algorithms, and reinforcement machine learning algorithms. Furthermore, the machine learning model is trained by interpreting patterns in the training dataset and adjusting the machine learning algorithms accordingly to get a desired output. Alternatively, or in addition, certain adjustable parameters in the image analysis software, such as in a pattern recognition subroutine, to compare images may be given more weight by the software if they are more representative of or sensitive to features identifying the log than other adjustable parameters. A few high-quality photographs from the harvesting site may be fed in as input images, optionally as a supplement to the routine pre-recorded image(s). Such images are expected to give a higher correlation with images at the sorting station when the corresponding log reaches the sorting station, and hence provide direction for the image analysis software.

Optionally, the data processing arrangement or the imaging device comprises means to down-sample the images and the data processing arrangement executes the image analysis software to compare images pixel by pixel (or by pattern matching or patch matching) to obtain a correlation of the pre-recorded image(s) and the newly captured image.

This may include means to repeatedly realign images to be compared in stepwise fashion until optimum correlation is reached. A database of past correlations is maintained to allow refinement of specifications for correlations that indicate a match.

According to an embodiment, the system further comprises a data memory device having a second machine learning model, wherein the data processing arrangement is further configured to train the second machine learning model to determine the log quality level by use of the second set of images as a part of a training dataset. The second machine learning model is employed by the data processing arrangement to determine the log quality. Optionally, the second set of images are employed as the training dataset as the second set of images are captured by placing each of the first end and the second end of the given log close to the plurality of imaging devices and thereby have high resolution images.

Furthermore, the data processing arrangement is configured to append the log identification information associated with the given log with the determined plurality of physical characteristics of the given log in the database arrangement. The determined plurality of physical characteristics, such as determined log quality and log volume data, are appended to the log identification information to enable storing of all information related to the given log in the database arrangement for retrieval of information in future use such as subsequent steps.

According to an embodiment, a buffer storage stage that stores the given log after the sorting stage and before the given log enters the sawmill stage, the data processing arrangement is configured to:
receive at least one image of the first end or the second end of the given log from a portable image-capture device associated with a certification control authority;
compare the received at least one image with an image database of the database arrangement; and
verify a fell place of the given log and other log data based on the log identification information associated with the given log for certification, wherein the log identification information is accessed based on a successful match of features at the comparison of the received at least one image with corresponding image in the image database, wherein verification information is communicated to the portable image-capture device for the certification. Optionally, the system simplifies the certification process for the certification control authority. Optionally, the certification control authority is operable to provide certification to the given log at any of the subsequent stage of the wood processing chain. In an example, the certification control authority is able to provide certification to the given log before the given log enters the sawmill stage. Optionally, verification information after certification is also appended to the log identification information so that the certification provided by the certification control authority is accessible at a later stage and enables the customers to have trust on the authenticity of the wood-based products delivered to them from the entity producing the wood-based products from the logs.

According to an embodiment, the system further comprises a downstream imaging device implemented at least one subsequent stage of the wood processing chain, including a sawmill stage of the wood processing chain, wherein the downstream imaging device is configured to capture at least one image of the first end or the second end of the given log. The downstream imaging device is a camera that is configured to capture at least one image of the first end or the second end of the given log. The term "sawmill stage" refers to a stage in the wood processing chain in which the logs, from the sorting station, is processed and cut into lumber (or planks). The downstream imaging device is configured to capture the at least one image to initiate detection of the given log at the sawmill stage. According to an embodiment, the database arrangement also comprises an image database and image analysis software. The image analysis software when executed by the data processing arrangement causes the captured image of the first end (or the second end) of the given log captured by the downstream imaging device to be compared with the images stored in the image database of the database arrangement. According to an embodiment, the data processing arrangement is further configured to retrieve the log identification information associated with the given log at, at least one subsequent stage, optionally at each subsequent stage, of the wood processing chain based on the captured at least one image of the first end or the second end of the given log so as to track processing of the given log from the harvesting site to sorting station and further to the at least one subsequent stage including the sawmill stage in the wood processing chain. Moreover, the data processing arrangement may be further configured to compare an individual quality level of a plank of the given log with the log quality level of the given log stored in the database arrangement to increase quality prognosis of planks of wood. The features associated with the given log are extracted from the at least one image of the first end or the second end of the given log and further compared with the features of the given log stored in the database arrangement. Moreover, based on the comparison of the features the log identification information associated with the given log is retrieved, and thus processing of the given log from the harvesting site to sorting station and further to the sawmill stage is trackable in the wood processing chain. According to an embodiment, a display module coupled to the database arrangement is configured to display log identification information associated with the given log in response to a successful match of the least one image based on the comparison by the image analysis software. According to an embodiment, the log identification information associated with the given log is received from the database arrangement and follows the log throughout the cutting process at the sawmill stage. Thus, each plank or other cut wood piece obtained after cutting the given log is assigned the log identification information, so that even a plank or other cut wood piece obtained from the given log is identifiable through the whole value chain to the final consumer.

Optionally, as described above, the sorted logs after exit from the sorting stage are stored in the buffer storage for weeks or months. In an implementation, a new image of the first end or the second end of the given log captured by the downstream imaging device, such as at the sawmill stage, has higher resolution than the images taken earlier in the process (e.g. at the buffer storage space, the sorting stage, or the harvesting stage). As the number of specific identifications, e.g. marks in the end face (i.e. the first end or the second end) of the given log increases in the sawmill stage, thus when the given log is cut, there is a higher likelihood to identify the specific planks from a specific log as compared to logs without any specific identifications. Thus, in other words, a last captured image at a previous stage may act as an identification image for a next stage, where the identification image is potentially used for comparison with the newly captured image at the next stage (e.g. the sawmill stage) to identify a given log or a plank from the given log. Moreover, the at least one image of the first end or the second end of the given log captured by the downstream imaging device may replace or complement already existing images of the given log in the database arrangement. Moreover, quality prognosis of wood is potentially improved by using more cameras (i.e. downstream imaging devices) in the sawmill station. Quality information is stored in the database arrangement based on the images captured at the fell place (i.e. the harvesting stage) and in the sorting station. Optionally, based on the captured images of the cut planks, the individual quality level of each plank is compared with the quality level of the given log stored in the database arrangement. Such comparison over a time period is potentially used to improve the quality prognosis.

The present disclosure also relates to the method for tracking logs in a wood processing chain, wherein the method is implemented in a system comprising a database arrangement, a plurality of imaging devices, and a data processing arrangement, wherein the method comprises:

capturing, by the plurality of imaging devices, a first set of images that includes at least one image of a first end and at least one image of a second end of a given log from at least a first prespecified oblique angle with respect to a longitudinal axis in a direction of a length of the given log towards the log, wherein the first prespecified oblique angle is within a defined threshold range;

identifying, by the data processing arrangement, the given log at the sorting station based on at least the captured first set of images and at least one pre-recorded image of the first end or the second end of the given log at the harvesting site in the wood processing chain;

comparing the at least one pre-recorded image of the first end or the second end of the given log at the harvesting site with the captured first set of images at the sorting station in the database arrangement, in order to find an optimum image from the compared images for identification of the given log;

determining, by the data processing arrangement, a plurality of physical characteristics of the given log at the sorting station based on at least the first set of images; and appending the log identification information associated with the given log with the determined plurality of physical characteristics of the given log in the database arrangement.

Various embodiments and variants disclosed above apply mutatis mutandis to the method.

Notably, the method optionally further comprises the following steps:

capturing, by the plurality of imaging devices, a first set of images that includes at least one image of a first end and at least one image of a second end of an unrecorded log, for which there is no pre-recorded image, from at least a first prespecified oblique angle with respect to a longitudinal axis in a direction of a length of the unrecorded log towards the log, wherein the first prespecified oblique angle is within a defined threshold range;

identifying, by the data processing arrangement, the unrecorded log at the sorting station based on at least the captured first set of images and log identification information of neighbouring logs as they enter the sorting station;

determining, by the data processing arrangement, a plurality of physical characteristics of the unrecorded log at the sorting station based on at least the first set of images; and appending the log identification information associated with the unrecorded log with the determined plurality of physical characteristics of the unrecorded log in the database arrangement.

The log identification information may include batch identification.

Optionally, the method further comprises capturing, by the plurality of imaging devices, a second set of images of the given log from a second angle that corresponds to an angle-of-capture of the given log in the at least one pre-recorded image at the harvesting site.

Optionally, the method further comprises training a second machine learning model to determine the log quality level by use of the second set of images as a part of a training dataset, wherein the second machine learning model is stored in a data memory device of the system.

Optionally, the method further comprises determining, by the data processing arrangement, a length and/or volume of the given log at the sorting station based on the first set of images that are captured from the first prespecified oblique angle with respect to the horizontal axis in the direction of a length of the given log, wherein the determined length and/or volume is one of the plurality of physical characteristics of the given log.

Optionally, the method further comprises:

determining, by the data processing arrangement, a log quality level of the given log at the sorting station based on at least one of the first set of images or the second set of images, wherein the determined log quality level is one of the plurality of physical characteristics of the given log. Moreover, the method may comprise comparing a quality level of a plank of the given log with the log quality level of the given log stored in the database arrangement to increase quality prognosis of wood.

Optionally, the method further comprises:

capturing, by a downstream imaging device, at least one image of the first end or the second end of the given log, wherein the downstream imaging device is implemented at, at least one subsequent stage including a sawmill stage of the wood processing chain; and retrieving, by the data processing arrangement, the log identification information associated with the given log at the at least one subsequent stage of the wood processing chain based on the captured at least one image of the first end or the second end of the given log so as to track processing of the given log from the harvesting site to sorting station and further to the at least one subsequent stage including the sawmill stage in the wood processing chain.

DETAILED DESCRIPTION OF THE DRAWINGS

Referring to FIG. 1A, there is shown a block diagram of a system 100A to track logs in a wood processing chain, in accordance with an embodiment of the present disclosure. As shown, the system comprises a database arrangement 102, a plurality of imaging devices 104 and a data processing arrangement 106. Moreover, the data processing arrangement 106 is communicatively coupled to the database arrangement 102, and the plurality of imaging devices 104.

Figure 1B:
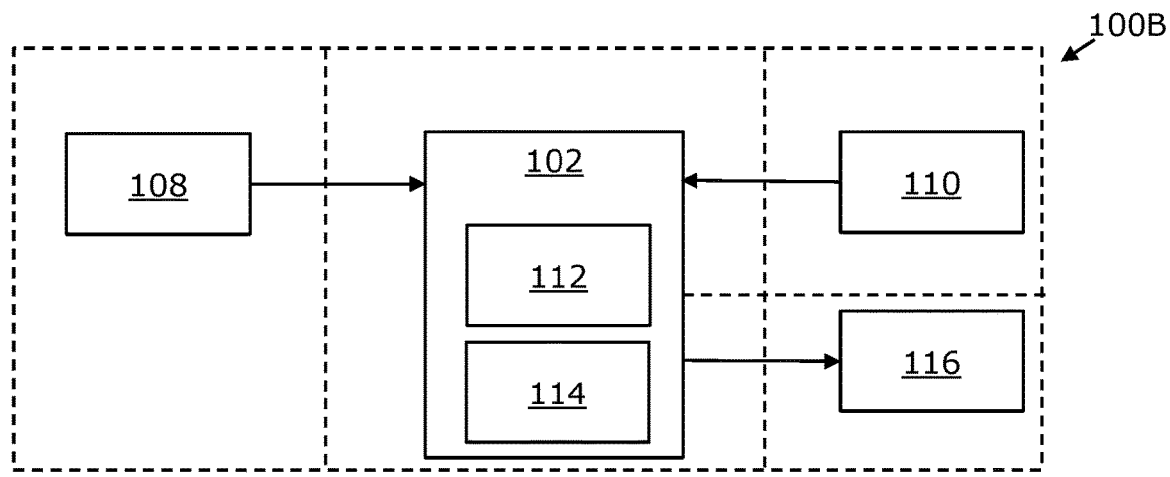
FIG. 1B is a block diagram of a system to track logs in a wood processing chain, in accordance with another embodiment of the present disclosure.

Referring to FIG. 1B, there is shown a block diagram of a system 100B to track logs in a wood processing chain, in accordance with another embodiment of the present disclosure. As shown, the system comprises an imaging device 108 at a harvesting site, used to capture an image of an end of a given log as it passes through. The captured image is stored as a pre-recorded image in an image database 112 of the database arrangement 102. Further, shown is a downstream imaging device 110, implemented at a sawmill stage of the wood processing chain, which is used to capture an image of the first end (or the second end) of the given log. Moreover, a plurality of imaging devices (not shown) implemented at a sorting station is configured to capture a first set of images of the given log. Furthermore, the first set of images of the given log potentially replaces the pre-recorded image of the given log in the database arrangement 102. As shown, the database arrangement 102 comprises an image database 112 and image analysis software 114. The image analysis software 114 when executed by the data processing arrangement 106 causes the captured image of the first end (or the second end) of the given log captured by the downstream imaging device 110 to be compared (for match finding) with the images stored in the image database 112 of the database arrangement 102. Moreover, a display module 116 coupled to the database arrangement 102 is configured to display log identification information associated with the given log in response to a successful match of image based on the comparison by the image analysis software 114.

Figure 2A:
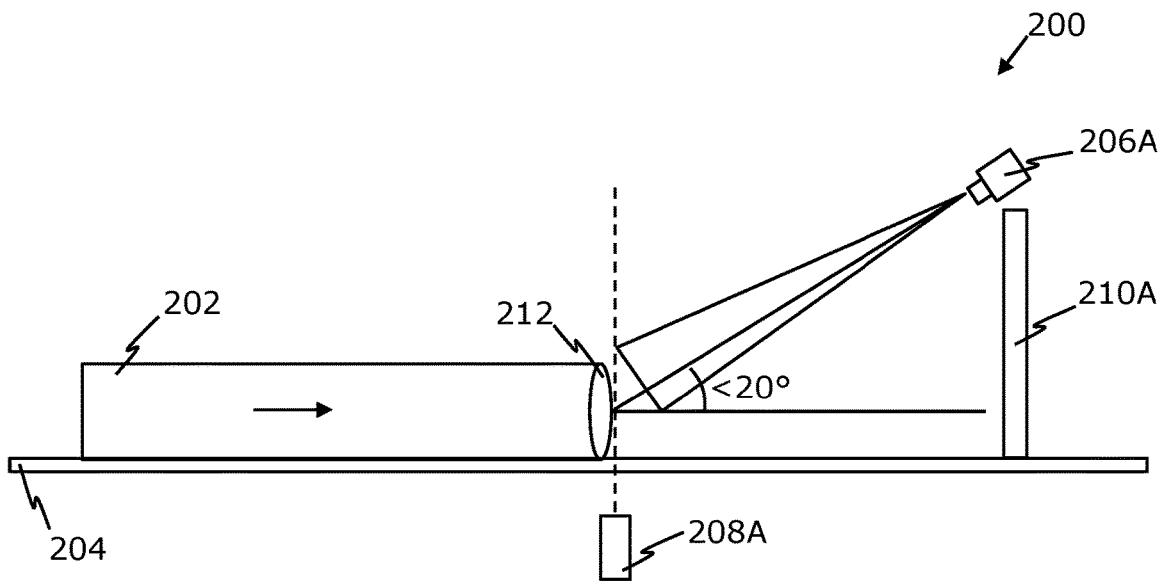
FIGS. 2A to 2D collectively illustrate an exemplary implementation of a system at a sorting station to track logs in a wood processing chain, in accordance with an embodiment of the present disclosure.

Referring to FIGS. 2A to 2D, there is shown an exemplary implementation of a system 200, at a sorting station, to track logs in a wood processing chain, in accordance with an embodiment of the present disclosure. In each figure, an arrow indicates the direction of movement of the log. Referring to FIG. 2A, the system 200 comprises a given log 202, a conveyor 204 on which the given log 202 moves in the sorting station, a first imaging device 206A, and a first sensor 208A. The first imaging device 206A is positioned at a first location 210A at the sorting station. Moreover, the first imaging device 206A at the first location 210A is activated to capture a first image (not shown) when a first end 212 (i.e. front end) of the given log 202 passes the first sensor 208A at the time of movement along the conveyor 204.

Figure 2B:
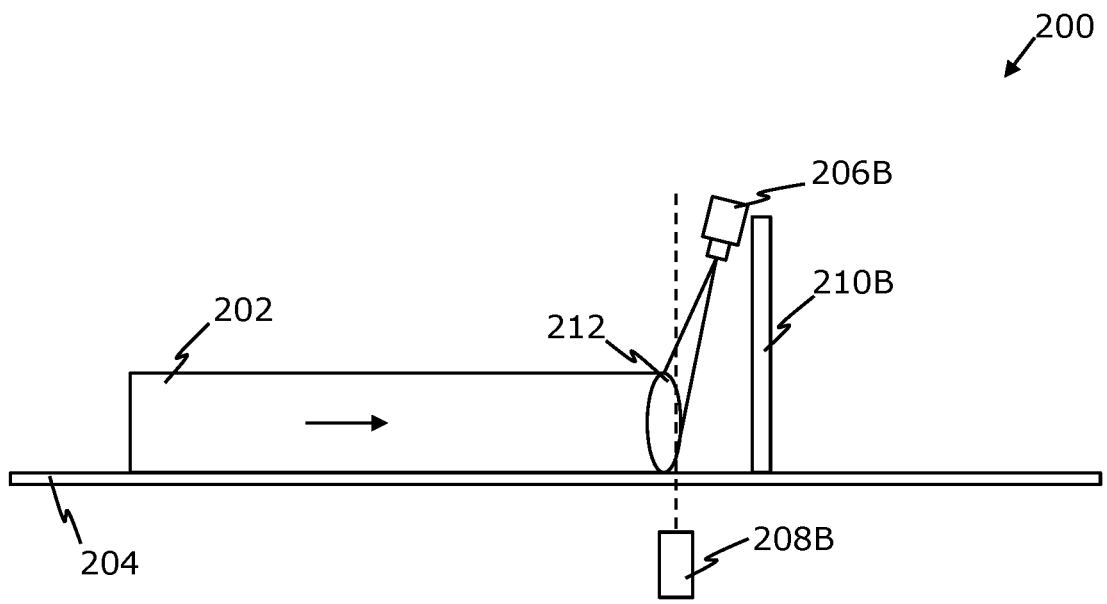

Referring to FIG. 2B, there is shown a second imaging device 206B, and a second sensor 208B. The second imaging device 206B is positioned at a second location 210B at the sorting station. Moreover, the second imaging device 206B at the second location 210B is activated to capture a second image (not shown) when the first end 212 of the given log 202 passes the second sensor 208B at the time of movement along the conveyor 204.

Figure 2C:
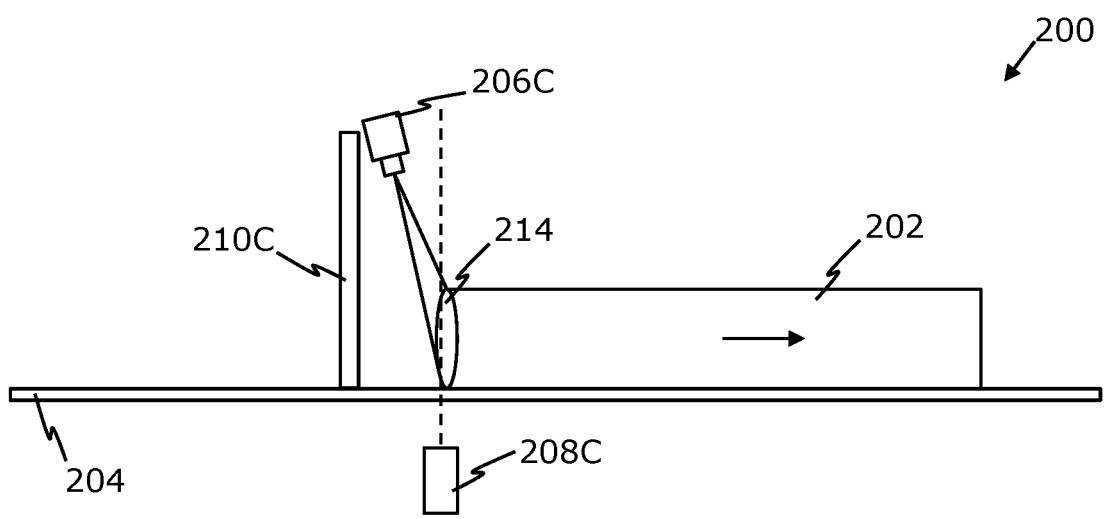

Referring to FIG. 2C, there is shown a third imaging device 206C, and a third sensor 208C. The third imaging device 206C is positioned at a third location 210C at the sorting station. Moreover, the third imaging device 206C at the third location 210C is activated to capture a third image (not shown) when a second end 214 of the given log 202 passes the third sensor 208C at the time of movement along the conveyor 204.

Figure 2D:
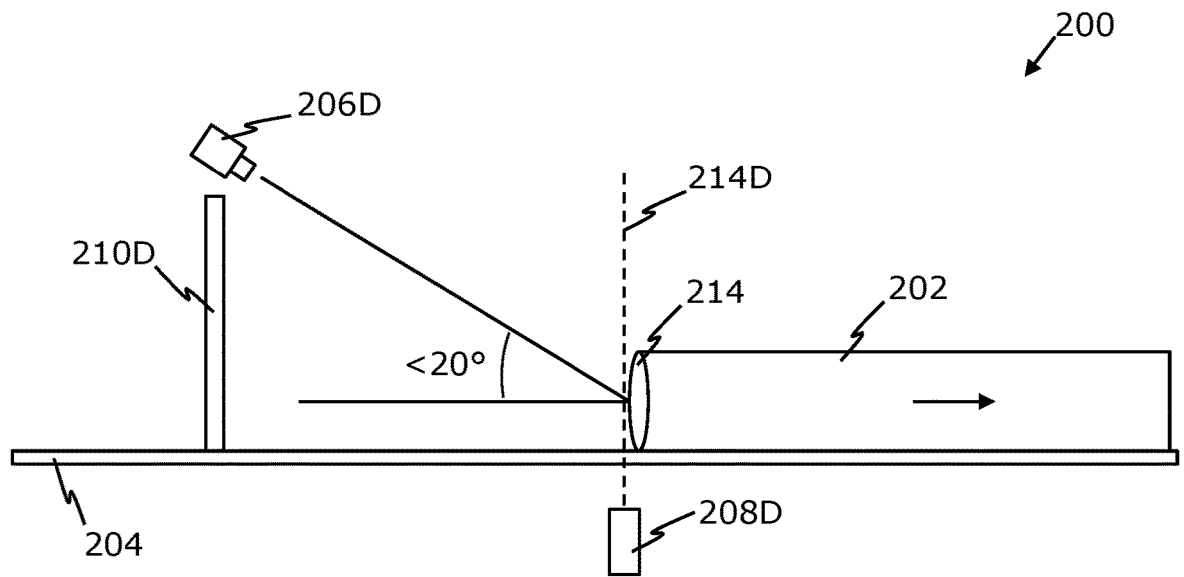

Referring to FIG. 2D, there is shown a fourth imaging device 206D, and a fourth sensor 208D. The fourth imaging device 206D is positioned at a fourth location 210D at the sorting station. Moreover, the fourth imaging device 206D at the fourth location 210D is activated to capture a fourth image (not shown) when the second end 214 of the given log 202 passes the fourth sensor 208D at the time of an exit from the sorting station.

Figure 3:
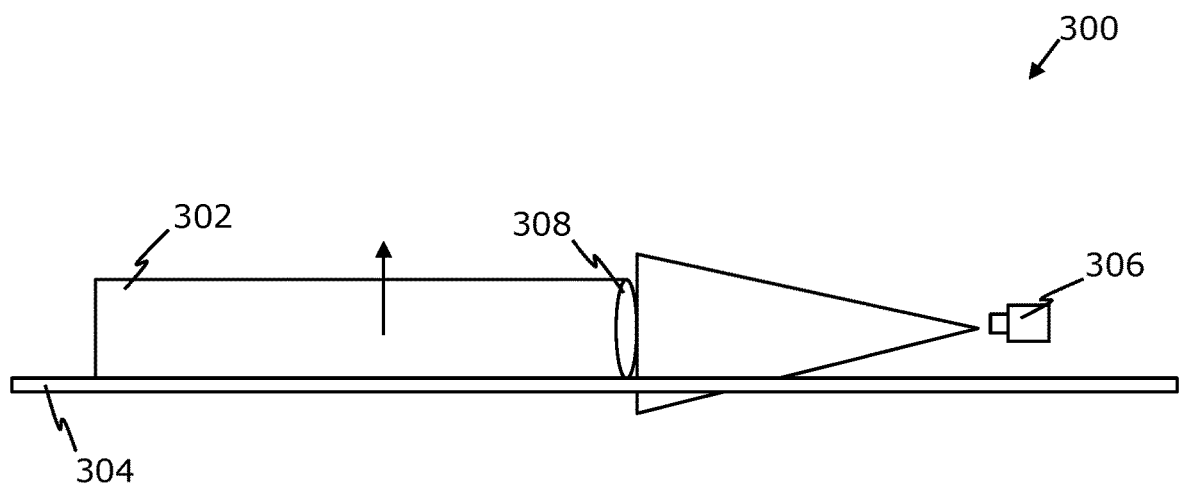
FIG. 3 is an exemplary implementation of a system at a sawmill stage to track logs in a wood processing chain, in accordance with an embodiment of the present disclosure.

Referring to FIG. 3, there is shown an exemplary implementation of a system 300, at a sawmill stage, to track logs in a wood processing chain, in accordance with an embodiment of the present disclosure. As shown, the system comprises a given log 302, a conveyor 304 on which the given log 302 moves in the sawmill stage. The system 300 comprises a downstream imaging device 306 implemented at the sawmill stage of the wood processing chain. The downstream imaging device 306 is configured to capture at least one image (not shown) of the first end 308 of the given log, which is used to match images stored in a database arrangement, and if a match is found, log identification information associated with the given log 302 is retrieved and the given log 302 is identified and further tracked. The log may be removed vertically as indicated by the arrow.

Figure 4:
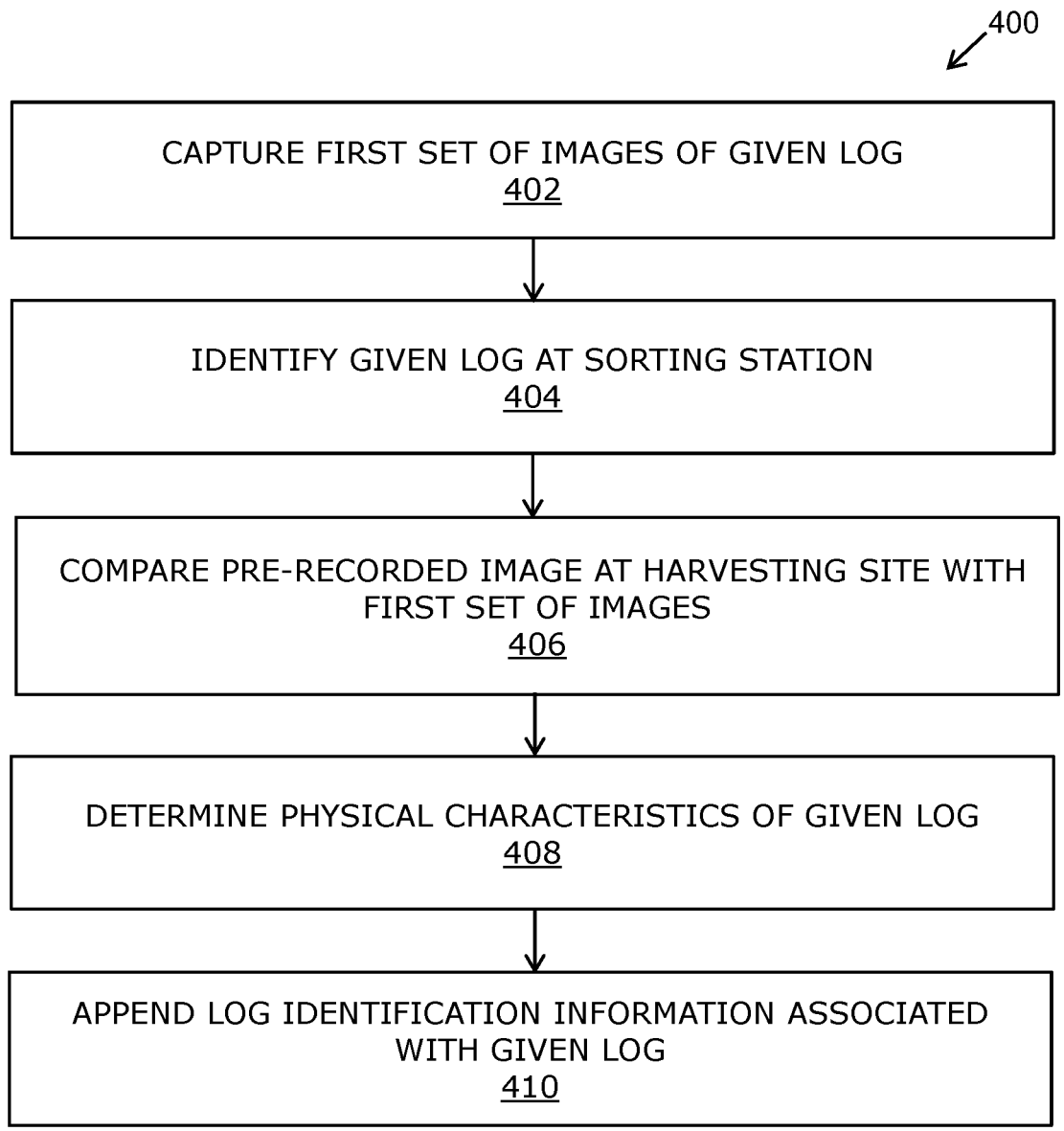
FIG. 4 is an illustration of steps of a method for tracking logs in a wood processing chain, in accordance with an embodiment of the present disclosure.

Referring to FIG. 4, there is shown an illustration of steps of a method 400 for tracking logs in a wood processing chain, in accordance with an embodiment of the present disclosure. The method is implemented in a system comprising a database arrangement, a plurality of imaging devices, and a data processing arrangement. At a step 402, a first set of images that includes at least one image of a first end and at least one image of a second end of a given log is captured by the plurality of imaging devices from at least a first prespecified oblique angle with respect to a longitudinal axis in a direction of a length of the given log towards the log, wherein the first prespecified oblique angle is within a defined threshold range. At a step 404, the given log at the sorting station is identified by the data processing arrangement based on at least the captured first set of images and at least one pre-recorded image of the first end or the second end of the given log at the harvesting site in the wood processing chain. At a step 406, the at least one pre-recorded image of the first end or the second end of the given log at the harvesting site is replaced with the captured first set of images at the sorting station in the database arrangement. At a step 408, a plurality of physical characteristics of the given log at the sorting station is determined by the data processing arrangement based on at least the first set of images. At a step 410, the log identification information associated with the given log is appended with the determined plurality of physical characteristics of the given log in the database arrangement.

The steps 402 to 410 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system to track logs in a wood processing chain, the system comprises:
- a database arrangement comprising at least one pre-recorded image of a first end or a second end of a given log at a harvesting site in the wood processing chain, wherein the given log is associated with log identification information;
- a plurality of imaging devices implemented at a sorting station, wherein the plurality of imaging devices are configured to:
- capture a first set of images that includes at least one image of the first end and at least one image of the second end of the given log from at least a first prespecified oblique angle with respect to a longitudinal axis in a direction of a length of the given log towards the log, wherein the first prespecified oblique angle is within a defined threshold range;
- a data processing arrangement communicatively coupled to the database arrangement and the plurality of imaging devices, wherein the data processing arrangement is configured to:
- identify the given log at the sorting station based on at least the captured first set of images;
- compare the at least one pre-recorded image of the first end or the second end of the given log at the harvesting site with the captured first set of images at the sorting station in the database arrangement, in order to find an optimum image from the compared images for identification of the given log;
- determine a plurality of physical characteristics of the given log at the sorting station based on at least one of the first set of images; and
- append the log identification information associated with the given log with the determined plurality of physical characteristics of the given log in the database arrangement; and
- a data memory device having a first machine learning model, wherein the data processing arrangement is configured to train the first machine learning model for identification of a new log when the new log enters the sorting station, wherein the identification is executed by the first machine learning model based on a similarity of features between a newly captured image of a first end or a second end of the new log at the sorting station and the corresponding pre-recorded images of the first end or the second end of the new log captured at the harvesting site.

2. A system according to claim 1, wherein the data processing arrangement is configured to replace the at least one pre-recorded image of the first end or the second end of the given log at the harvesting site with the captured first set of images at the sorting station in the database arrangement.

3. A system according to claim 1, wherein the system further comprises a set of sensors, wherein a first imaging device of the plurality of imaging devices is positioned at a first location at the sorting station, and
wherein the first imaging device at the first location is activated to capture a first image of the first set of images when the first end of the given log passes a first sensor of the set of sensors at the time of movement along a conveyor, wherein the first image includes the first end of the given log.

4. A system according to claim 3, wherein the data processing arrangement is further configured to determine a log quality level of the given log at the sorting station based on at least one of the first set of images or the second set of images, wherein the determined log quality level is one of the plurality of physical characteristics of the given log.

5. A system according to claim 4, wherein the system further comprises a data memory device having a second machine learning model, wherein the data processing arrangement is further configured to train the first machine learning model to determine the log quality level by use of the second set of images as a part of a training dataset.

6. A system according to claim 1, wherein the plurality of imaging devices are further configured to capture a second set of images of the given log from a second angle that corresponds to an angle-of-capture of the given log in the at least one pre-recorded image at the harvesting site.

7. A system according to claim 6, wherein a second imaging device of the plurality of imaging devices at a second location at the sorting station is configured to capture a second image that corresponds to one of the second set of images when the first end of the given log further passes a second sensor of the set of sensors at the time of movement along a conveyor, wherein the second image includes the first end of the given log.

8. A system according to claim 6, wherein a third imaging device of the plurality of imaging devices at a third location at the sorting station is configured to capture a third image that corresponds to one of the second set of images when the second end of the given log further passes a third sensor of the set of sensors at the time of movement along the conveyor, wherein the third image includes the second end of the given log.

9. A system according to claim 6, wherein a fourth imaging device of the plurality of imaging devices at a fourth location at the sorting station is configured to capture a fourth image that corresponds to the at least one image of the second end from the first set of images when the second end of the given log further passes a fourth sensor of the set of sensors at the time of an exit from the sorting station, wherein the fourth image includes the second end of the given log.

10. A system according to claim 1, wherein the data processing arrangement is further configured to determine a length and/or a volume of the given log at the sorting station based on the first set of images that are captured from the first prespecified oblique angle with respect to the longitudinal axis in the direction of the length of the given log towards the log, wherein the determined length and/or the volume is one of the plurality of physical characteristics of the given log.

11. A system according to claim 1, wherein the system further comprises a downstream imaging device implemented at, at least one subsequent stage of the wood processing chain, including a sawmill stage of the wood processing chain, wherein the downstream imaging device is configured to capture at least one image of the first end or the second end of the given log; and
the data processing arrangement is further configured to:
retrieve the log identification information associated with the given log at the at least one subsequent stage of the wood processing chain based on the captured at least one image of the first end or the second end of the given log so as to track processing of the given log from the harvesting site to sorting station and further to the at least one subsequent stage including the sawmill stage in the wood processing chain.

12. A system according to claim 1 wherein in a buffer storage stage that stores the given log after the sorting stage and before the given log enters the sawmill stage, the data processing arrangement is configured to:

receive at least one image of the first end or the second end of the given log from a portable image-capture device associated with a certification control authority; and compare the received at least one image with an image database of the database arrangement; and verify a fell place of the given log and other log data based on the log identification information associated with the given log for certification, wherein the log identification information is accessed based on a successful match of features at the comparison of the received at least one image with corresponding image in the image database, wherein verification information is communicated to the portable image-capture device for the certification.

13. A method for tracking logs in a wood processing chain, wherein the method is implemented in a system comprising a database arrangement, a plurality of imaging devices, and a data processing arrangement, wherein the method comprises:
   capturing, by the plurality of imaging devices a first set of images that includes at least one image of a first end and at least one image of a second end of a given log from at least a first prespecified oblique angle with respect to a longitudinal axis in a direction of a length of the given log towards the log, wherein the first prespecified oblique angle is within a defined threshold range;
   identifying, by the data processing arrangement, the given log at the sorting station based on at least the captured first set of images and at least one pre-recorded image of the first end or the second end of the given log at the harvesting site in the wood processing chain;
   comparing the at least one pre-recorded image of the first end or the second end of the given log at the harvesting site with the captured first set of images at the sorting station in the database arrangement, in order to find an optimum image from the compared images for identification of the given log;
   determining, by the data processing arrangement, a plurality of physical characteristics of the given log at the sorting station based on at least the first set of images; and
   appending the log identification information associated with the given log with the determined plurality of physical characteristics of the given log in the database arrangement; and
   training a first machine learning model for identification of a new log when the new log enters the sorting station, wherein the identification is executed by the first machine learning model based on a similarity of features between a newly captured image of a first end or a second end of the new log at the sorting station and the corresponding pre recorded images of the first end or the second end of the new log captured at the harvesting site.

14. A method according to claim 13, further comprising replacing the at least one pre-recorded image of the first end or the second end of the given log at the harvesting site with the captured first set of images at the sorting station in the database arrangement.

15. A method according to claim 13, further comprising capturing, by the plurality of imaging devices, a second set of images of the given log from a second angle that corresponds to an angle-of-capture of the given log in the at least one pre-recorded image at the harvesting site.

16. A method according to claim 15, further comprising training a second machine learning model to determine the log quality level by use of the second set of images as a part of a training dataset, wherein the second machine learning model is stored in a data memory device of the system.

17. A method according to claim 15, further comprising determining, by the data processing arrangement, a length and/or volume of the given log at the sorting station based on the first set of images that are captured from the first prespecified oblique angle with respect to the horizontal axis in the direction of a length of the given log, wherein the determined length and/or volume is one of the plurality of physical characteristics of the given log.

18. A method according to claim 13, further comprising determining, by the data processing arrangement, a log quality level of the given log at the sorting station based on at least one of the first set of images or the second set of images, wherein the determined log quality level is one of the plurality of physical characteristics of the given log.

19. A method according to claim 13, further comprising:
   capturing, by a downstream imaging device, at least one image of the first end or the second end of the given log, wherein the downstream imaging device is implemented at, at least one subsequent stage including a sawmill stage of the wood processing chain; and
   retrieving, by the data processing arrangement, the log identification information associated with the given log at the at least one subsequent stage of the wood processing chain based on the captured at least one image of the first end or the second end of the given log so as to track processing of the given log from the harvesting site to sorting station and further to the at least one subsequent stage including the sawmill stage in the wood processing chain.

* * * * *